United States Patent
Ha et al.

(10) Patent No.: US 9,517,187 B2
(45) Date of Patent: Dec. 13, 2016

(54) IMPLANT COATED WITH NET-SHAPED OR ISLAND-SHAPED LOW-CRYSTALLIZED HYDROXYAPATITE AND METHOD FOR COATING SAME

(75) Inventors: Kyung Won Ha, Seoul (KR); Gyu Ok Choi, Seoul (KR)

(73) Assignee: Osstemimplant Co., Ltd., Seoul (KR)

( * ) Notice: Subject to any disclaimer, the term of this patent is extended or adjusted under 35 U.S.C. 154(b) by 344 days.

(21) Appl. No.: 13/378,029

(22) PCT Filed: May 18, 2010

(86) PCT No.: PCT/KR2010/003132
§ 371 (c)(1),
(2), (4) Date: Dec. 22, 2011

(87) PCT Pub. No.: WO2010/147308
PCT Pub. Date: Dec. 23, 2010

(65) Prior Publication Data
US 2012/0088100 A1 Apr. 12, 2012

(30) Foreign Application Priority Data
Jun. 18, 2009 (KR) .................. 10-2009-0054315

(51) Int. Cl.
| | |
|---|---|
| *A61L 33/00* | (2006.01) |
| *A61K 6/04* | (2006.01) |
| *A61C 8/00* | (2006.01) |
| *A61L 27/06* | (2006.01) |
| *A61L 27/32* | (2006.01) |

(Continued)

(52) U.S. Cl.
CPC .............. *A61K 6/04* (2013.01); *A61C 8/0013* (2013.01); *A61K 6/0017* (2013.01); *A61K 6/033* (2013.01); *A61L 27/06* (2013.01); *A61L 27/32* (2013.01); *A61L 2420/02* (2013.01); *A61L 2430/02* (2013.01); *A61L 2430/12* (2013.01); *Y10T 428/265* (2015.01)

(58) Field of Classification Search
CPC .... A61C 8/0013; A61L 27/06; A61L 2430/12; A61L 2430/02; A61L 2420/02; A61L 27/32; A61K 6/04; A61K 6/0017; A61K 6/033; Y10T 428/265
USPC ........................................ 427/2.24
See application file for complete search history.

(56) References Cited

U.S. PATENT DOCUMENTS

| | | | |
|---|---|---|---|
| 6,207,218 B1 * | 3/2001 | Layrolle et al. | ............ 427/2.27 |
| 2008/0097618 A1 * | 4/2008 | Baker et al. | ............... 623/23.51 |

FOREIGN PATENT DOCUMENTS

| | | |
|---|---|---|
| CN | 1106765 A | 8/1995 |
| CN | 1442120 A | 9/2003 |
| CN | 1486752 A | 4/2004 |

(Continued)

OTHER PUBLICATIONS

Xie et al. "Nanometer-scale Surface Modification of Ti6AI4V Alloy for Orthopedic Applications" Journal of Biomedical Materials Research Part A, available online Jun. 28, 2007.*

(Continued)

*Primary Examiner* — Robert S Walters, Jr.
(74) *Attorney, Agent, or Firm* — Seed IP Law Group LLP (57) ABSTRACT

The present disclosure relates to a method for coating a surface of a titanium implant with low crystalline hydroxyapatite having network- or island-like morphology and to an implant coated by such method.

10 Claims, 7 Drawing Sheets

(51) Int. Cl.
*A61K 6/00* (2006.01)
*A61K 6/033* (2006.01)

(56) References Cited

FOREIGN PATENT DOCUMENTS

| CN | 101340935 A | 1/2009 |
| JP | 11-323570 A | 11/1999 |
| KR | 2003-0087664 A | 11/2003 |
| KR | 10-2004-0099964 A | 12/2004 |
| KR | 20-2009-0002577 U | 3/2009 |

OTHER PUBLICATIONS

Baker et al., "Nanocomposite hydroxyapatite formation on a Ti-13Nb-13Zr alloy exposed in a MEM cell culture medium and the effect of $H_2O_2$ addition," *Acta Biomaterialia* 5:63-75, 2009.
Tamura et al., "Hydroxyapatite Film Coating by Thermally Induced Liquid-phase Deposition Method for Titanium Implants," *Dental Materials Journal* 25(1): 32-38, 2006.

* cited by examiner

| | Length (pm) | | Angle (deg) | |
|---|---|---|---|---|
| | HA | Coating | HA | Coating |
| a | 187.00 | 185.44 | 53.89 | 53.30 |
| b | 223.66 | 226.99 | 57.57 | 58.36 |
| c | 184.40 | 180.62 | 68.75 | 67.56 |
| a' | 187.82 | 185.37 | 54.18 | 54.38 |
| b' | 222.18 | 226.36 | 57.16 | 57.81 |
| c' | 202.62 | 196.46 | 66.19 | 67.24 |

IMPLANT COATED WITH NET-SHAPED OR ISLAND-SHAPED LOW-CRYSTALLIZED HYDROXYAPATITE AND METHOD FOR COATING SAME

BACKGROUND

Technical Field

The present disclosure relates to the field of coated titanium implants, which have been widely used as grafting materials. The present disclosure relates in particular to a method for coating a surface of a titanium implant with low crystalline hydroxyapatite having bioabsorbability, and to an implant coated by such a method.

Description of the Related Art

In recent years, hydroxyapatite has been widely used as an artificial biomaterial capable of replacing hard tissues such as bones or teeth. Hydroxyapatite is a material that is chemically and crystallographically identical to mineral components which constitute bones and teeth in the human body. When transplanted into the human body, hydroxyapatite exhibits high biocompatibility with the surrounding cells and rapidly forms a chemical bond directly with bones at the junction region. A pure hydroxyapatite crystal composed of calcium ions, phosphate ions, and hydroxyl ions is a stoichiometric crystal having a rod-like structure and has a high crystallinity. On the other hand, a biocrystal isolated from bones or calcified cartilage is a nonstoichiometric hydroxyapatite which has a low crystallinity (see J. C. Elliott, In Structure and Chemistry of the Apatites and Other Calcium Orthophosphates, *Studies in Inorganic Chemistry* 18, Amsterdam: Elsevier, pp 111-190 (1994)).

Titanium has been widely used as an implant material due to having physical properties similar to those of human bones and excellent mechanical strength. Further, titanium has been extensively used as a biological metal since it does not cause inflammatory responses or other immune responses in vivo. In order to impart bioactivity to titanium for industrial applications, titanium is subjected to a variety of surface modifications such as blasting, acid etching, and the like (see numerous patent documents including Korean Patent Application No. 98-23075). However, titanium disadvantageously exhibits poor biocompatibility as compared to ceramic materials such as hydroxyapatite, and undergoes dissolution of metal ions upon long term residence thereof in the human body, which consequently results in the formation of in vivo inorganic substances.

For these reasons, there have recently been developed a variety of methods for obtaining a biomaterial having both excellent mechanical strength and biocompatibility for use in replacement of biological hard tissues by coating titanium with a hydroxyapatite thin film. Conventional representative methods of coating a ceramic, thereby imparting bioactivity to a surface of titanium, may include plasma spraying, sputtering, ion implantation, ion beam deposition, and the like. In order to form a crystalline film in which crystallographical properties of hydroxyapatite are similar to those of biocrystals, various approaches using a calcium phosphate solution or a simulated body fluid have been undertaken.

Plasma spraying which has been most commonly used among the above-mentioned methods has shortcomings such as non-uniformity of a coating layer due to instantaneous exposure to a high temperature of 10,000° C. or higher, and a difficulty to achieve a coating having a thickness of less than about 10 μm. Further, this method has a problem of very low biological reactivity in that hydroxyapatite coated on the surface of titanium undergoes decomposition in vivo due to a very high crystallinity or is refractory to removal by osteoclasts. Further, this method is known to involve simultaneous formation of calcium phosphates or calcium hydroxides having different phases as by-products (see H.-G. Pfaff, et al., Properties of HA-Coatings in 'Bioceramics', vol. 6, P. Ducheyne and D. Christiansen, Eds., pp. 419-424, Butterworth-Heinemann Ltd. (1993)). Generally, bones in the human body undergo a series of processes named as Bone Remodeling where an old bone is removed from the skeleton and a new bone is added. A hydroxyapatite coating film having a high crystallinity does not take part in the remodeling process of bones. Accordingly, hydroxyapatite remains as a coating film for a long period of time in the human body. Even after a functional bone is generated, the coating film exists and decomposes into by-products having different phases, which contributes to peeling of the coating film from the surface, finally resulting in the separation of an implant. To this end, there is a need for the development of low crystalline hydroxyapatite which is capable of taking part in a remodeling process of bones through the in vivo absorption by osteoclasts, thereby overcoming problems of conventional hydroxyapatite coating layers having high crystallinity.

Further, sputtering or ion implantation, apart from high-priced equipment for this purpose, has suffered from various problems such as complex shapes, poor uniformity of the coating layer formed on irregular parts, and detachment of implants due to the peeling-off phenomenon in the human body.

On the other hand, as a wet coating method, there is a method using a calcium phosphate solution or a simulated body fluid. Preparation or coating of various types of calcium phosphates is started from a calcium phosphate ion solution. These calcium phosphate compounds can be prepared by mixing calcium ions and phosphate ions in an aqueous solution under a variety of conditions. In this connection, it is known that the type and form of compounds are greatly affected by ion concentrations, Ca/P ratios and pH conditions (see Ayako Oyane, Kazuo Onuma, Tadashi Kokubo, and Atsuo Ito *J. Phys. Chem. B* 1999, 103, 8230-8235; J. C. Elliott, In Structure and Chemistry of the Apatites and Other Calcium Orthophosphates, *Studies in Inorganic Chemistry* 18, Amsterdam: Elsevier, pp 111-190 (1994)). The above-exemplified coating processes involve complicated steps or require a long coating time. Generally, it is difficult for a supersaturated solution of calcium phosphate to maintain a constant concentration, due to spontaneous precipitation (see H. B. Wen, et al., *J. Biomed. Mater. Res.* 41, 227-236(1998)). Further, a process which is performed under a limited condition of maintaining about 37° C. may take a long period of time, about one month or more, depending on conditions of the surface. In order to solve these problems, there have been developed methods of coating an implant with calcium phosphate by lowering the process temperature and applying a buffer system of phosphate ions to thereby inhibit the precipitation of calcium phosphate crystals in a supersaturated solution. However, these methods also require the use of acids for the manufacture of a calcium ion solution and a phosphate ion solution, and the adjustment of pH (hydrogen ion concentration) by admixture with a base solution at a low temperature for the inhibition of calcium phosphate precipitation. In addition, these methods also do not overcome limitations of a complex and long process time (Korean Patent Application No. 1999-38528 to Kim Hyun-Man, et al., and Korean Patent Application No. 2000-51923 to Kim Se-Won, et al., both assigned to Oscotec Inc.), since it needs for example, purification (by porous filtration or centrifugation) for removing amorphous calcium phosphate which is generated at the beginning of mixing the calcium ion solution and the phosphate ion solution.

Calcium phosphate compounds using a wet method have different equilibrium phases, depending on temperatures and pH values. In particular, at a temperature of 40° C. or lower, calcium phosphate has an equilibrium phase of amorphous ($Ca_3(PO_4)_2 \cdot nH_2O$; n=3 to 4.5) or nonstoichiometric hydroxyapatite ($Ca_{10-x}(HPO_4)_x(PO_4)_{6-x}(OH)_{2-x} \cdot nH_2O$; x=0 to 1, n=0 to 2) at a pH of 7 or higher, an equilibrium phase of octacalcium phosphate (OCP, $Ca_8H_2(PO_4)_6 \cdot 5H_2O$) at a pH of 6 to 7, and an equilibrium phase of dicalcium phosphate (DCP, $CaHPO_4$), dicalcium phosphate dihydrous (DCPD, $CaHPO_4 \cdot 2H_2O$) or the like at a pH of 6 or lower. The calcium phosphate coating according to a conventional wet method is based on change of calcium phosphate solubility, taking advantage of the fact that the solubility of calcium phosphate decreases as the reaction temperature increases. Therefore, an initial process should proceed at a low temperature of 2° C. to 5° C., and it is very difficult to obtain a coating film of calcium phosphate as well as a colloidal solution of calcium phosphate without the elevation of temperature. Further, during the process in which the colloidal solution and coating film of calcium phosphate are obtained by elevating reaction temperature, a pH of the solution is generally terminated in the range of 6.0 to 6.5. Even though an accurate equilibrium phase of the calcium phosphate coating film according to the conventional wet method has not been fully understood, it seems to be OCP based on the correlation between the temperature and the pH of the calcium phosphate solution.

As discussed above, conventional wet coating methods utilize differences in the solubility of calcium phosphate in response to changes in temperature, and thus are limited by the need to control temperature and/or pH, the need to use elevated reaction temperature, and the complex procedures required for formation of calcium phosphate coating films. Accordingly, the present disclosure provides solutions and alternatives to the complexity of the procedure exhibited by the conventional wet method.

BRIEF SUMMARY

The present disclosure provides methods for coating titanium or titanium alloy implants with hydroxyapatite and implants coated by such methods. The methods disclosed can achieve superior productivity by relatively simple processes at low cost, without requiring temperature and/or pH control or elevated temperatures. The implants coated by the methods disclosed herein may show superior incorporation into bone and may thus have improved properties and lifespan over implants coated by conventional methods.

Titanium or titanium alloy implants coated by the methods disclosed herein include dental implants. Titanium or titanium alloy implants coated by the methods disclosed herein may also include any of a variety of implants known in the art for use with bone, including plates, screws, nails, wires, or pins. Such implants may be useful for repairing, replacing or strengthening bone, for example, bone that has been damaged.

Implant coating methods described herein provide low crystalline hydroxyapatite-coated implants that may be used for long periods of time while not being isolated from new bone, such that the implants are absorbed by osteoclasts in vivo, thereby taking part in remodeling processes of bone. Methods and implants disclosed herein thereby overcome limitations of conventional methods for forming hydroxyapatite coating layers having high crystallinity and the resulting implants.

Further, coating methods providing low crystalline hydroxyapatite according to the present invention are relatively simple compared to conventional wet methods. The coating methods are also economically favorable due to the absence of requirements for strict control of reaction conditions such as temperature and/or pH and for elevation of reaction temperature, while imparting excellent bioactivity.

Implants formed according to coating methods disclosed herein have an advantage of being usable for a long period of time while not being isolated from new bones, in such a way that the implant is absorbed by osteoclasts in vivo, thereby taking part in a remodeling process of bones.

Further, an implant coating method according to the present disclosure is capable of enhancing success of a titanium implant in such a way that the bioactivity imparted to a surface of the implant results in strong interfacial bonding between the implant and bone tissues or teeth tissues, and the promotion of osteoconductivity or osteogenesis. Furthermore, separation of an implant resulting from peeling of the surface coating layer is prevented due to bioabsorbability of the coating layer formed from low crystalline hydroxyapatite.

Further, an implant coating method according to the present disclosure enables the production of an excellent dental implant by very simple processes at low cost. The method allows control of thickness and morphology of the coating layer, as necessary, such as a thin coating layer, a thick coating layer, and co-exposed surfaces of titanium and a coating layer. Therefore, the present invention can be applied to a variety of biomaterial fields in accordance with desired uses, for example, the orthopedic area as well as the dental area.

According to one possible embodiment, a method is provided for coating an implant, wherein the method includes pretreating a surface of a titanium or titanium alloy implant; adding each of a phosphate ion solution and a calcium ion solution to the pretreated titanium or titanium alloy implant; and dipping and storing the titanium or titanium alloy implant in the calcium phosphate solution for 1 hour or more. The resulting thin film of low crystalline hydroxyapatite may have a network- or island-like morphology and may be bioabsorptive.

BRIEF DESCRIPTION OF THE SEVERAL VIEWS OF THE DRAWINGS

Objects, features and other advantages of the present invention will be more clearly understood from the following detailed description taken in conjunction with the accompanying drawings, in which.

DETAILED DESCRIPTION

The present disclosure relates to an implant and method in which hydroxyapatite having excellent bone growth and osteoconductivity is coated on a surface of titanium having excellent mechanical properties for use as an implant. The present disclosure provides a technique which induces a growth of network-like or island-like low crystalline hydroxyapatite on a surface of a titanium implant in a low-concentration calcium phosphate aqueous solution at room temperature of 15° C. to 30° C.

The coating method disclosed herein is also applicable to implants using a titanium alloy, rather than pure titanium, as a raw material, or implants using titanium as a raw material and then being surface-treated by a variety of methods. Even though the process time may be slightly different from the embodiment of the present invention, depending on the type of surface treatments, the reaction time can be easily controlled by those skilled in the art to which a technique of coating an implant surface with hydroxyapatite pertains.

According to one embodiment, the implant coating method includes pretreating a surface of a titanium or titanium alloy implant; adding each of a phosphate ion solution and a calcium ion solution to the pretreated titanium or titanium alloy implant; and dipping and storing the titanium or titanium alloy implant in the calcium phosphate solution for 1 hour or more.

The pretreatment step may be carried out by a variety of methods commonly used in the art, such as a Resorbable Blasting Media (RBM) method in which surface treatment is carried out using resorbable blasting media, a Sand-blasted Large grit, and Acid etched (SLA) surface treatment method in which aluminum blasting is followed by acid etching, heat treatment at a temperature of 300° C. or higher, anodization, and heat treatment of surface after acid or base treatment. When a titanium or titanium alloy material which was surface-treated by any of the above-mentioned methods is used, the pretreatment step may be omitted. Further, the pretreatment step preferably includes ultrasonic treatment of the titanium or titanium alloy implant in distilled water, a calcium ion solution, a phosphate ion solution or a calcium phosphate solution for 1 minute or more. The ultrasonic treatment may also be carried out after the above-mentioned RBM, SLA or heat treatment and the like is performed.

In the pretreatment step, with regard to an implant composed of the above-mentioned titanium or titanium alloy as a raw material, any hydrocarbon remaining on a surface of the implant may be optionally removed using a nitric acid solution. The concentration of the nitric acid solution is preferably 4 v/v % to 60 v/v %. Depending on hydrophilic properties and morphology of the surface, the nitric acid cleaning process may be omitted. Following the nitric acid cleaning, the surface may be washed with distilled water in order to remove residual nitric acid on the surface. The distilled water washing may also be omitted for the surface which was not subjected to the nitric acid cleaning process.

A low-concentration (about 1.0mM to about 10mM) calcium ion solution proposed in the present specification can be prepared by a simple method of dissolving calcium nitrates(for example, $Ca(NO_3)_2$ or $Ca(NO_3)_2 \cdot 4H_2O$, etc.) or calcium chlorides (for example, $CaCl_2$ or $CaCl_2 \cdot 2H_2O$, etc.) in distilled water. A low concentration (about 1.0 mM to about 10 mM) phosphate ion solution of the present application can be prepared by a simple method of dissolving ammonium phosphates(for example, $(NH_4)_2HPO_4$, etc.) or sodium phosphates(for example, $Na_2HPO_4$ or $Na_2HPO_4 \cdot 2H_2O$ or $Na_2HPO_4 \cdot 7H_2O$, etc.) or potassium phosphates (for example, $K_2HPO_4$ or $K_2HPO_4 \cdot 3H_2O$, etc.) in distilled water.

The phosphate ion solution and the calcium ion solution are respectively added to an implant substrate. Alternatively, prior to application thereof to the implant substrate, these two solutions may be mixed to prepare a calcium phosphate solution which is then applied to the implant substrate. Preferably, each of two solutions is added to the implant substrate.

A concentration of the calcium phosphate solution is in the range of 1.0 mM to 10 mM. Further, even though a dipping time of the implant in the low-concentration calcium phosphate solution is 1 hour or more, the dipping time may vary depending on intended state and morphology of the surface, and a coating thickness. Further, the dipping temperature is in the range of about 10° C. to about 35° C., and preferably about 15° C. to about 30° C. The dipping temperature may be kept constant or elevated. Depending on intended uses and purposes, the dipping time and dipping temperature can be easily selected by those skilled in the art.

The calcium ion solution and the phosphate ion solution, which were prepared at a low concentration, are respectively added to the titanium implant, followed by dipping for 1 hour or more, and the titanium implant is removed and briefly washed with distilled water, whereby low crystalline hydroxyapatite having network- or island-like morphology can be coated on a titanium or titanium alloy implant surface.

The coating method according to the present invention has advantages in that there is no need to control a pH of the calcium phosphate solution. It is not necessary to stir for mixing of the phosphate ion solution and the calcium ion solution.

Methods of coating low crystalline hydroxyapatite proposed in the present disclosure are based on sufficient utilization of a phenomenon in which a solubility of the calcium phosphate solution is lowered at room temperature and a chemical mechanism in which mixing calcium ions with the phosphate ion solution causes changes in a dissociation constant of hydrogen phosphate ($HPO_4^{2-}$) in the phosphate ion solution, resulting in continuous production of amorphous or crystalline calcium phosphate during dipping of a titanium implant in the calcium phosphate solution. In an embodiment of the methods disclosed herein, the following is a reaction scheme of the phosphate ion solution.

$$Na_2HPO_4 \rightarrow 2Na^+ + H(PO_4)^{2-}$$

$$H(PO_4)^{2-} \leftrightarrow H^+ + (PO_4)^{3-} (Ka=10^{-11.66})$$

A dissociation constant of hydrogen phosphate ions in the phosphate ion solution is very low. Therefore, there is a very small amount of a dissociated form of hydrogen phosphate ions in the solution. Unlike the conventional methods which take advantage of a buffer or temperature-dependent solubility of calcium phosphate, the methods of the present disclosure make use of changes in dissociation constant of hydrogen phosphate ions occurring during a mixing process of the calcium ion solution and the phosphate ion solution. An addition of the calcium ion solution to the phosphate ion solution accelerates the dissociation of hydrogen phosphate ions. Even though the dissociation of hydrogen phosphate ions takes place continuously and may vary to some extent depending on the concentration of the ion solutions or reaction temperature, the dissociation of hydrogen phosphate ions takes place rapidly around one hour after proceeding the reaction, and then the dissociation of hydrogen phosphate ions takes place slowly and continuously as time goes on. Accordingly, it is possible to obtain a coating film having a network-like morphology at the point where rapid dissociation of hydrogen phosphate ions takes place. When the process is allowed to proceed for a longer period of time (3 hours or more), it is possible to obtain a thick coating film of low crystalline hydroxyapatite due to continuous dissociation of hydrogen phosphate ions. The thin film of low crystalline hydroxyapatite has a thickness of about 10 nm or less. As dipping time increases, a thicker film can be obtained.

Pretreatment in the present disclosure is a process which imparts activity to the implant surface in order to secure uniform and high-adhesion coating of calcium phosphate crystals to a surface of the titanium implant in the calcium phosphate solution. Generally, a production rate of calcium phosphate crystals is very high in the calcium phosphate solution at room temperature. Therefore, if appropriate activity is not imparted to the titanium implant surface, a coating is not formed on the implant and/or adhesive strength of a coating to the implant is too lowered. In conclusion, the pretreatment of the titanium implant surface is needed to increase a generation and growth of crystalline calcium phosphates on the implant surface. Further, the pretreatment results in improved coating uniformity of low crystalline hydroxyapatite on the implant surface, and significantly improved repeatability and reproducibility.

The pretreatment method in the present disclosure is carried out as described hereinbefore, preferably by subjecting the titanium or titanium alloy implant to ultrasonic treatment in distilled water, a calcium ion solution, a phosphate ion solution or a calcium phosphate solution for one minute or more.

Low crystalline hydroxyapatite prepared by the coating method according to the present disclosure is characteristically nonstoichiometric and is also bioabsorptive.

Further, the low crystalline hydroxyapatite-coated implant of the present disclosure has a double surface with co-exposure of a network- or island-like coating layer and an implant titanium surface, whereby osteogenic capacity is improved due to synergistic effects between adhesion of titanium to cells and osteoconductive effects of hydroxyapatite.

As described herein, the coating of low crystalline hydroxyapatite having network- or island-like morphology in the calcium phosphate solution can determine a desired thickness depending on hydroxyapatites concentration, temperature and process time. A state of the coating can be confirmed under a scanning electron microscope. Due to the simplicity of the process, a coating degree of low crystalline hydroxyapatite can be appropriately controlled corresponding to desired applications in various implant areas as well as in teeth.

The following Examples provide particular embodiments related to the methods and implants described herein. These examples are provided only for illustration and should not be construed as limiting the scope and spirit of the present invention.

EXAMPLES

Example 1

Pretreatment of Titanium Implant

An SLA (surface treatment method including aluminum blasting followed by acid etching)-treated implant was dipped in a 12% nitric acid ($HNO_3$) solution for 5 minutes, followed by ultrasonic treatment, and the acid remaining on a surface of the implant was removed using distilled water ($H_2O$). The 12% nitric acid solution was prepared by mixing a 60% nitric acid solution and distilled water ($H_2O$) in a ratio of 1:4. The implant, from which surface impurities were removed by washing in the nitric acid solution, was dipped in distilled water, followed by ultrasonic treatment for 15 minutes.

Example 2

Preparation of Low-Concentration Calcium Ion Solution and Phosphate Ion Solution Preparation of a calcium phosphate solution was initiated from a step of preparing high-concentration 200 mM calcium (Ca) ion solution and phosphate ($PO_4$) ion solution. The high-concentration calcium ion solution was prepared by dissolving calcium chloride ($CaCl_2$) in distilled water ($H_2O$), and the high-concentration phosphate ion solution was prepared by dissolving sodium hydrogen phosphate ($Na_2HPO_4$) in distilled water ($H_2O$). The high-concentration 200 mM calcium ion solution and phosphate ion solution were respectively diluted to 5 mM by the addition of distilled water. 5 mM calcium ion solution and 5 mM phosphate ion solution were stored at the same temperature at which a coating process was to be carried out. Preferably, the calcium ion solution and the phosphate ion solution were stored in an incubator where the coating process was to be carried out.

Example 3

Low Crystalline Hydroxyapatite Coating

The low crystalline hydroxyapatite coating was prepared by placing an implant, which had been finally pretreated in distilled water, in a reaction container to which 5 mM low-concentration phosphate ion solution and 5 mM calcium ion solution were each sequentially added in an equal volume and mixed to prepare a 2.5 mM calcium phosphate solution. The reaction container containing the titanium implant and the 2.5 mM calcium phosphate solution was stored in an incubator at 20° C. for 60 minutes. Thereafter, the titanium implant was removed from the reaction container, washed briefly with distilled water, and dried to form a network-like coating surface.

Figure 3:
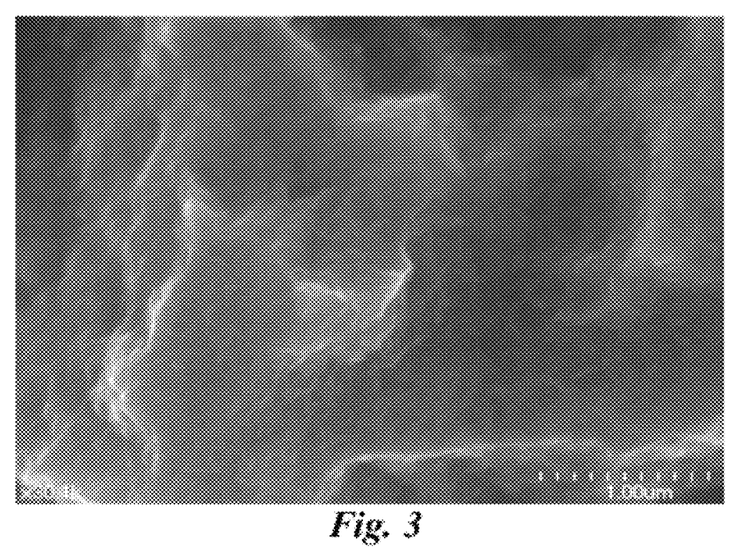
FIG. 3 is a scanning electron micrograph illustrating a thin coating of low crystalline hydroxyapatite having network- and island-like morphology on a titanium implant surface.
Figure 5:
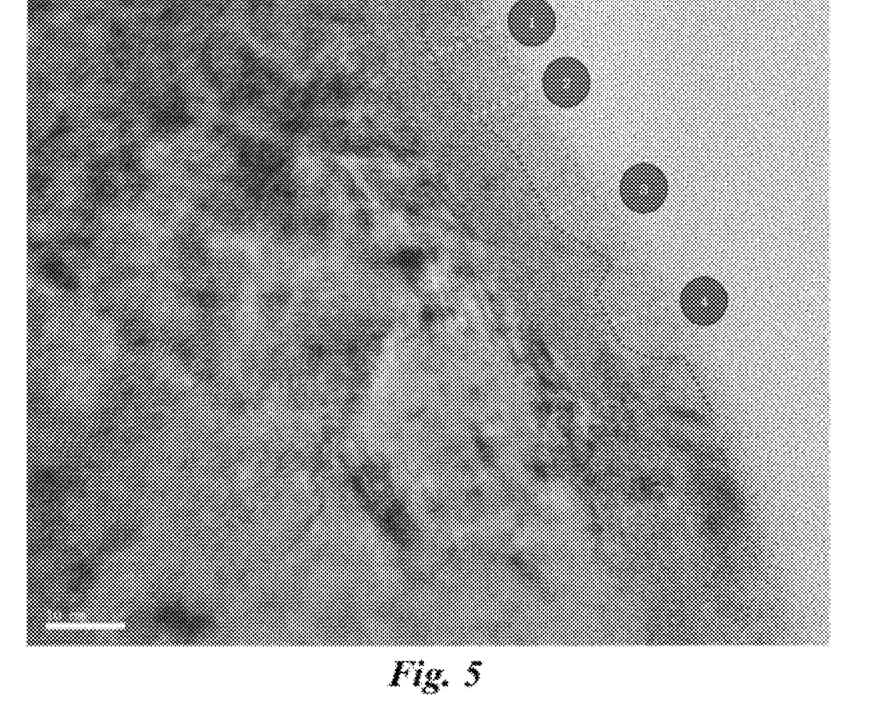
FIG. 5 is a transmission electron micrograph illustrating a thin coating film of low crystalline hydroxyapatite having network- and island-like morphology on a titanium implant surface.

A scanning electron micrograph of FIG. 3 shows a network-like coating surface and dual-surface of low crystalline hydroxyapatite and titanium. From a transmission electron micrograph of FIG. 5, it can be confirmed that the coating of low crystalline hydroxyapatite with network-like morphology has a thickness of 10 nm or less.

In order to adjust a thickness of the coating, the implant can be stored in an incubator for 180 minutes or more to form a thick coating of low crystalline hydroxyapatite. When the calcium phosphate solution is first prepared and 1 to 3 minutes later the pretreated implant is placed and stored in a reaction container for 60 minutes, it may also obtain an island-like coating surface externally existing as both titanium and low crystalline hydroxyapatite.

TABLE 1

Figure 1:
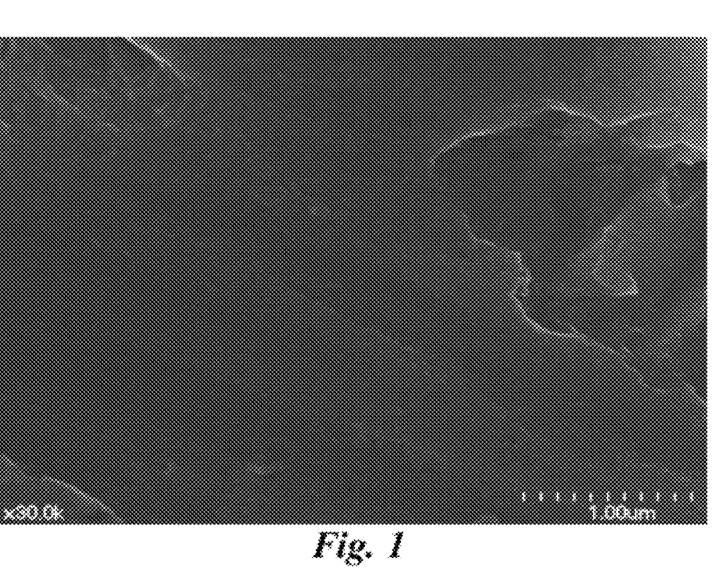
FIG. 1 is a scanning electron micrograph of a non-coated titanium implant surface.
Figure 2:
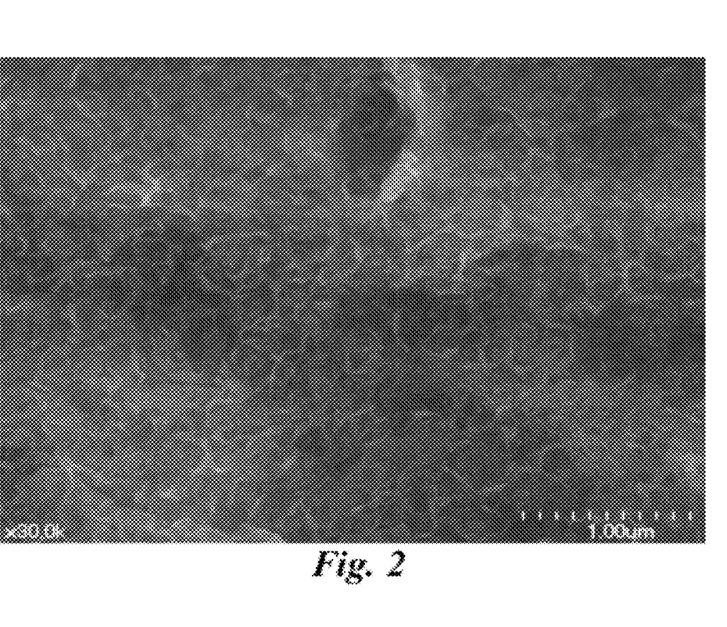
FIG. 2 is a scanning electron micrograph illustrating a thick coating of low crystalline hydroxyapatite having network-like morphology on a titanium implant surface.
Figure 4:
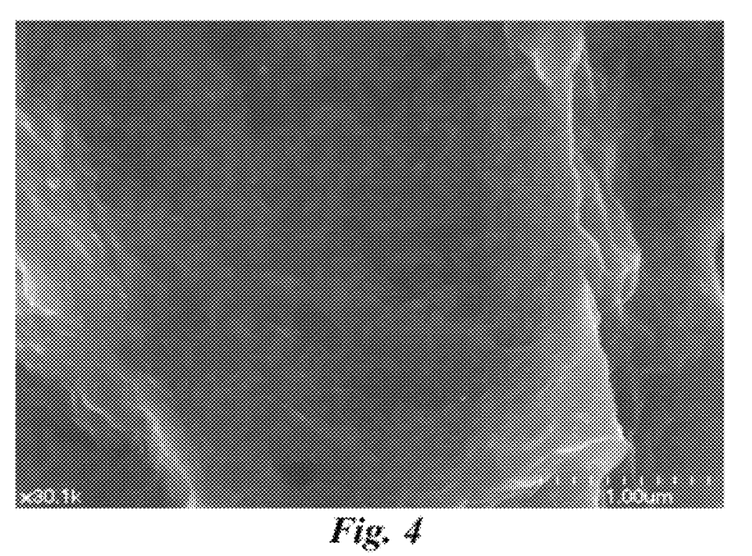
FIG. 4 is a scanning electron micrograph illustrating a coating of low crystalline hydroxyapatite having island-like morphology on a titanium implant surface.

|  | Thin network- & island-like morphology | Thick network-like morphology | Island-like morphology |
|---|---|---|---|
| Implant Pretreatment | Product Yes | Product Yes | Product Yes |
| Waiting time after mixing of solutions | 0 min | 0 min | 3 min |
| Concentration | 2.5 mM | 2.5 mM | 2.5 mM |
| Temperature | 20° C. | 20° C. | 20° C. |
| Time | 60 min | 180 min | 60 min |
| Results (drawings) | See FIG. 3 | See FIG. 2 | See FIG. 4 |

Comparative Example 1

Coatability of Titanium Implant According to Pretreatment

For an experimental group which was ultrasonic-pretreated in distilled water as in Example 1 and a non-pretreated control group, titanium implants were treated as in the procedure of Example 2 and Example 3.

TABLE 2

|  | Experimental group | Control group |
|---|---|---|
| Implant Pretreatment | Product Yes | Product No |
| Concentration | 2.5 mM | 2.5 mM |
| Temperature | 20° C. | 20° C. |
| Time | 60 min | 60 min |
| Results | Network-like morphology | Coating failed |

Figure 6:
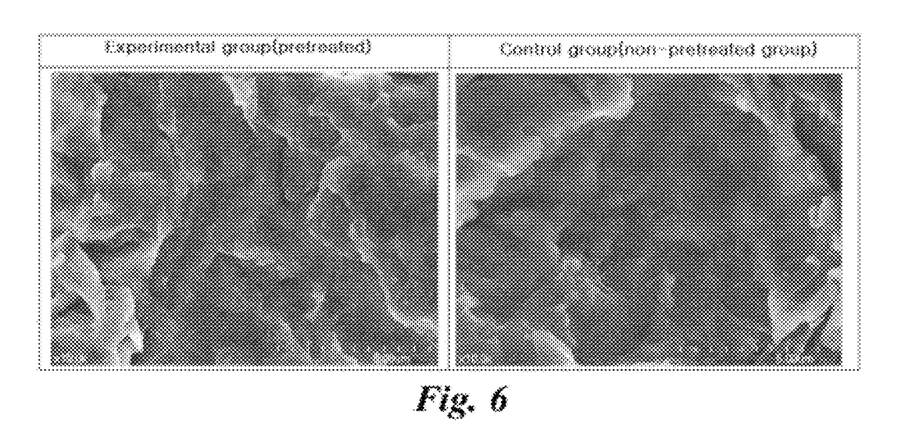
FIG. 6 is a scanning electron micrograph comparing the coatability of low crystalline hydroxyapatite depending on the presence and absence of pretreatment.
Figure 7:
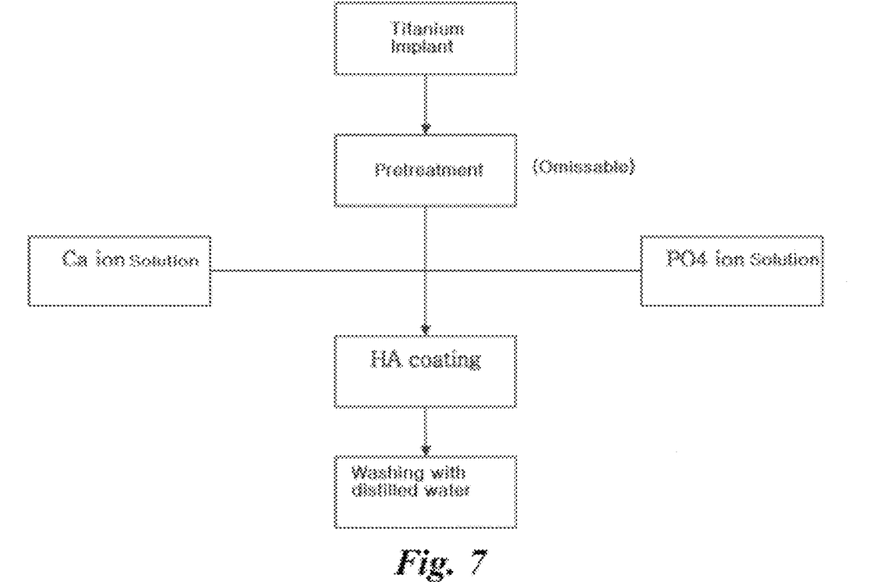
FIG. 7 is a schematic process flow chart of the present invention.
Figure 8:
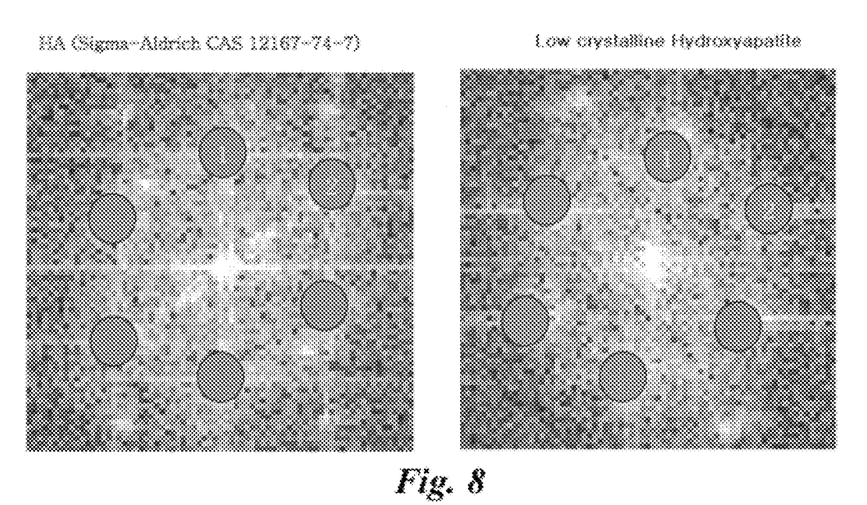
FIG. 8 is a comparison photograph of lattice structures observed through high-resolution transmission electron microscopy, between hydroxyapatite of Sigma Aldrich and a low crystalline hydroxyapatite coating surface according to the present invention.
Figure 9:
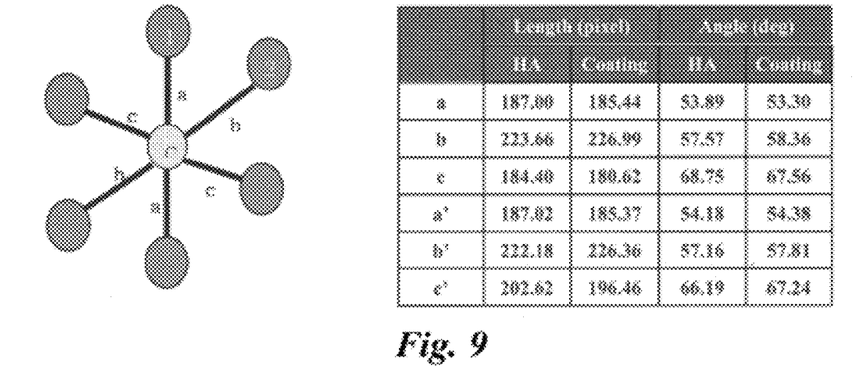
FIG. 9 shows measurement results for a distance from a center to individual atoms and an angle between individual atoms, obtainable from the lattice structure comparison photograph of FIG. 8.
Figure 10:
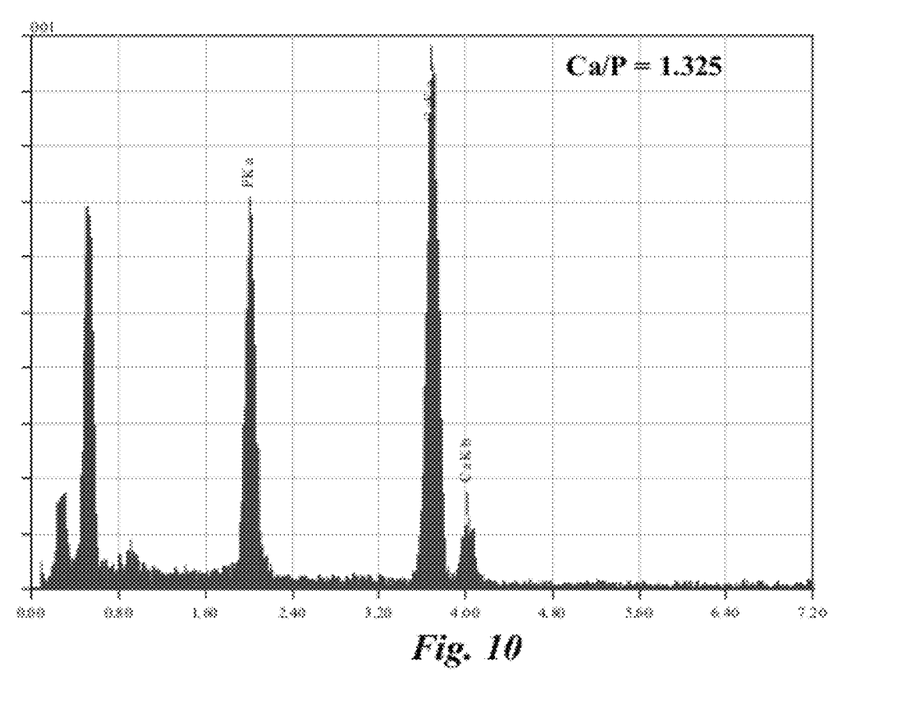
FIG. 10 shows results of low crystalline hydroxyapatite coated on a titanium implant measured by elemental analyzer under a high-resolution transmission electron microscope.

FIG. 6 is a scanning electron micrograph of the experimental group and the control group, confirming that the control group exhibits no formation of a coating, whereas the experimental group exhibits the formation of a thin coating film having network-like morphology. Therefore, the pretreatment is a factor which has an influence on the coatability in the titanium implant and is also capable of improving the uniformity of a coating film.

Experimental Example 1

Assay of Alkaline Phosphatase Activity of Mesenchymal Stem Cells

In order to measure a degree of differentiation of mesenchymal stem cells, which were cultured in a cell culture dish, into osteoblasts, activity of alkaline phosphatase (ALP) of the cells was assayed for the implants coated with low crystalline hydroxyapatite prepared in the above Example 3.

Human bone marrow-derived mesenchymal stem cells were seeded into a RBM (surface treatment method using resorbable blasting media)-treated titanium disc which was coated with low crystalline hydroxyapatite. A RBM-treated titanium disc was used as a control group. In order to induce differentiation of mesenchymal stem cells into osteoblasts, the cells were treated with a culture medium supplemented with 0.1 μM dexamethasone, 10 mM β-glycerol phosphate and 50 μg/ml ascorbic acid, followed by culture for 14 days, and alkaline phosphatase activities were assayed and compared each other. The cultured cells were washed with PBS, lysed with a lysis buffer, and assayed using an ALP activity assay kit.

Figure 11:
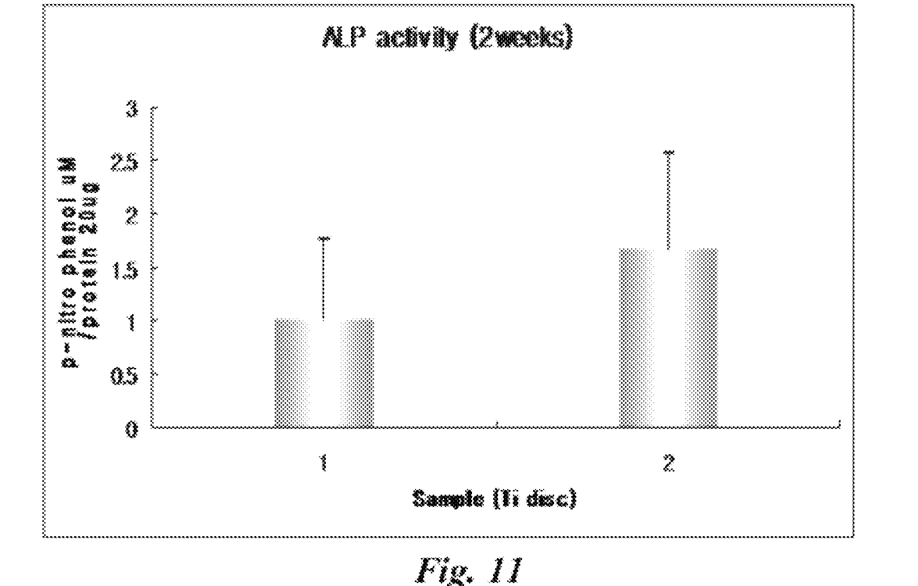
FIG. 11 is a graph comparing a degree of differentiation of mesenchymal stem cells into osteoblasts between an RBM-treated titanium substrate and a low crystalline hydroxyapatite-coated implant substrate, for 14 days.

As shown in a graph of FIG. 11, it can be confirmed that the alkaline phosphatase activity of mesenchymal stem cells was increased in the titanium disc coated with low crystalline hydroxyapatite having a mixed type of network-like morphology and island-like morphology prepared in the above-mentioned Example 3. From these results, it can be seen that the low crystalline hydroxyapatite-coated implant more greatly promotes the differentiation of mesenchymal stem cells into osteoblasts, as compared to the merely RBM (surface treatment method using resorbable blasting media)-treated implant used as a control group.

Experimental Example 2

Assay of Calcified Nodule Formation in Mesenchymal Stem Cells

In order to measure a degree of calcified nodule formation of mesenchymal stem cells which were cultured on a cell culture dish, the following experiment was carried out for the implants coated with low crystalline hydroxyapatite prepared in Example 3.

Human bone marrow-derived mesenchymal stem cells were seeded into a RBM (surface treatment method using resorbable blasting media)-treated titanium disc which was coated with low crystalline hydroxyapatite analogously to the procedure in Experimental Example 1. A RBM-treated titanium disc was used as a control group. In order to induce differentiation of the mesenchymal stem cells into osteoblasts, the cells were treated with a differentiation-inducing culture medium, followed by culture for 2 or 4 weeks. The cultured cells were washed with PBS, fixed with 4% paraformaldehyde for 15 minutes, and then washed with distilled water. An Alizarin Red solution (pH 4.2), which had been previously prepared, was added to the cells to perform a staining process for 20 minutes. The cells were then washed with distilled water to remove the non-stained solution. For quantitative evaluation of the stained calcified nodules, 10% w/v of cetylpyridinium chloride was added to a sodium phosphate solution (pH 7) to elute the stained dye which was then subjected to measurement of absorbance.

Figure 12:
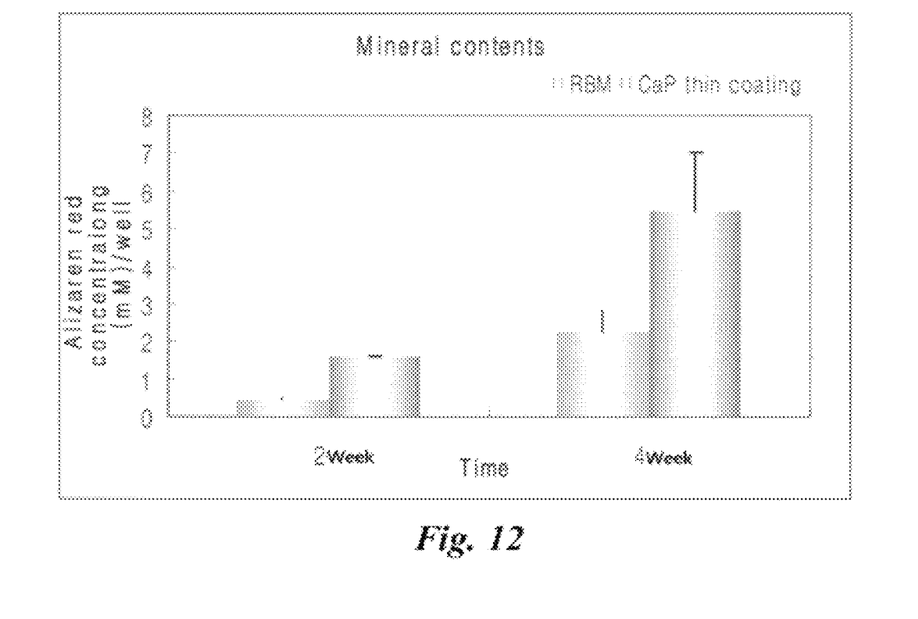
FIG. 12 is a graph comparing a degree of calcification of mesenchymal stem cells between an RBM-treated titanium substrate and a low crystalline hydroxyapatite-coated implant substrate, for 14 and 28 days, respectively.

As shown in a graph of FIG. 12, it can be seen that calcification of mesenchymal stem cells was increased on a surface of the titanium disc coated with low crystalline hydroxyapatite having a mixed type of network-like morphology and island-like morphology prepared in the above-mentioned Example 3. From these results, it can be seen that the low crystalline hydroxyapatite-coated implant more greatly promotes calcified nodule formation on the implant surface, as compared to the RBM (surface treatment method using resorbable blasting media)-treated implant used as a control group.

Experimental Example 3

Evaluation of Bioabsorbability in Animals

The implant coated with low crystalline hydroxyapatite prepared in Example 3 was transplanted into rabbit ilia and the survival of a coating film before and after bone remodeling was investigated.

A titanium implant, which was coated with low crystalline hydroxyapatite analogously to the procedure in Experimental Example 1, using an RBM (surface treatment method using resorbable blasting media)-treated titanium implant and a sample thereof as a base material, was transplanted into the ilium of a New Zealand white rabbit. The implant has a diameter of 3.5 mm and a length of 8.5 mm. For the grafting of the implant, the rabbit ilium was drilled to provide a hole with a diameter of 3.6 mm and the implant was manually pushed into the ilium. After 2 and 6 weeks, the rabbit was sacrificed, and the implant was removed from the rabbit and examined under a scanning electron microscope.

Figure 13:
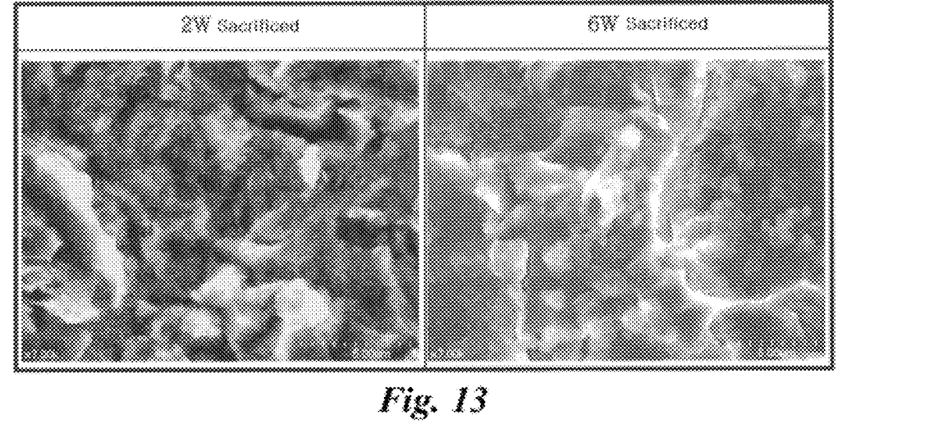
FIG. 13 is a scanning electron micrograph illustrating bioabsorbability of a coating film 2 and 6 weeks after transplantation of low crystalline hydroxyapatite.

The scanning electron micrograph given for comparative purposes in FIG. 13 shows that the coating film of nonstoichiometric low crystalline hydroxyapatite has bioabsorbability. In an experiment at the 2nd week after transplantation of the implant to the rabbit ilium, it was confirmed that the coating film still remains. In an experiment at the $6^{th}$ week, it was confirmed that the bone remodeling was already complete and therefore the coating film had disappeared due to osteoclasts. Accordingly, it can be seen that the nonstoichiometric low crystalline hydroxyapatite coating film of the present invention has bioabsorbability such that the hydroxyapatite coating film is removed by participation in the remodeling process of bones.

As can be seen from the Experimental Examples as described above, the implant coated with low crystalline hydroxyapatite having a mixed type of network-like morphology and island-like morphology promotes cellular differentiation and calcified nodule formation. Taken together, it can be confirmed that the low crystalline hydroxyapatite-coated implant of the present invention exhibits excellent biocompatibility. Further, it can be seen that the implant of the present invention can be used as a superior biomaterial that has bioabsorbability by participation thereof in a bone remodeling process, and ameliorates peeling of the coating film and consequent separation of the implant.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A method for coating a titanium or titanium alloy implant with hydroxyapatite, said method comprising:
   pretreating a surface of a titanium or titanium alloy implant,
   mixing a phosphate ion solution with a calcium ion solution to prepare a calcium phosphate solution, and
   dipping and storing the titanium or titanium alloy implant in the calcium phosphate solution for 1 hour to provide a titanium or titanium alloy implant having a double surface with co-exposure of a network- or island-like coating of hydroxyapatite and the implant surface.

2. The method according to claim 1, wherein the pretreatment step includes ultrasonic treatment of the titanium or titanium alloy implant in distilled water, a calcium ion solution, a phosphate ion solution or a calcium phosphate solution for 1 minute or more.

3. The method according to claim 2, further comprising washing the titanium or titanium alloy implant with an acidic solution before the ultrasonic treatment of the implant.

4. The method according to claim 3, wherein the acidic solution is a nitric acid solution.

5. The method according to claim 1, wherein the phosphate ion solution is prepared by dissolving ammonium phosphates, sodium phosphates or potassium phosphates in distilled water.

6. The method according to claim 1, wherein the calcium ion solution is prepared by dissolving calcium nitrate or calcium chloride in distilled water.

7. The method according to claim 1 or 2, wherein a reaction temperature in the step of dipping and storing the titanium or titanium alloy implant in the calcium phosphate solution is in the range of 15° C. to 30° C.

8. The method according to claim 1, wherein the pretreatment step is selected from the group consisting of an RBM (Resorbable Blasting Media) treatment, an SLA (Sandblasted Large grit, and Acid etched) treatment, a heat treatment at 300° C. or higher, an anodization, and a heat treatment after an acid or base treatment.

9. The method according to claim 1, wherein the calcium phosphate solution has a concentration of 1.0 mM to 10 mM.

10. The method according to claim 1, wherein the pretreatment step includes ultrasonic treatment of the titanium or titanium alloy implant in distilled water, a calcium ion solution, a phosphate ion solution or a calcium phosphate solution for 1 minute, after RBM (Resorbable Blasting Media) treatment, an SLA (Sand-blasted Large grit, and Acid etched) treatment, a heat treatment at 300° C. or higher, an anodization, or a heat treatment after an acid or base treatment.

* * * * *